(12) United States Patent
Rajasekharan et al.

(10) Patent No.: US 8,497,090 B2
(45) Date of Patent: Jul. 30, 2013

(54) FUNGAL STRAINS AND A PROCESS FOR PRODUCTION OF INSECTICIDE THEREOF

(75) Inventors: Ram Rajasekharan, Karnataka (IN); Chikkarasanahalli Shivegowda Vivekbabu, Karnataka (IN)

(73) Assignee: Indian Institute of Science, Karnataka (IN)

( * ) Notice: Subject to any disclaimer, the term of this patent is extended or adjusted under 35 U.S.C. 154(b) by 429 days.

(21) Appl. No.: 12/739,328

(22) PCT Filed: Oct. 22, 2008

(86) PCT No.: PCT/IN2008/000697
§ 371 (c)(1),
(2), (4) Date: Apr. 22, 2010

(87) PCT Pub. No.: WO2009/054003
PCT Pub. Date: Apr. 30, 2009

(65) Prior Publication Data
US 2010/0304441 A1    Dec. 2, 2010

(30) Foreign Application Priority Data
Oct. 23, 2007  (IN) .......................... 02392/CHE/2007

(51) Int. Cl.
*C12P 1/00*        (2006.01)

(52) U.S. Cl.
USPC ............................................ 435/41; 435/7.31

(58) Field of Classification Search
USPC .................................. 435/41, 7.31, 71.1, 171
See application file for complete search history.

(56) References Cited

U.S. PATENT DOCUMENTS
5,017,598 A    5/1991    Dowd et al.

FOREIGN PATENT DOCUMENTS
| JP | 07-138276 A | 5/1995 |
| JP | 2001-261610 A | 9/2001 |
| WO | 01-51605 A | 7/2001 |

OTHER PUBLICATIONS

Definition for pure, 1 page 2011.*
Definition for accession number, 1 page, 2009.*
These references were cited in the Written Opinion of the International Searching Authority (PCT/ISA/237) in PCT/IN2008/000697 dated Feb. 27, 2009.

* cited by examiner

*Primary Examiner* — Bin Shen
(74) *Attorney, Agent, or Firm* — Cowan, Liebowitz & Latman, P.C.; Mark Montague, Esq.

(57) ABSTRACT

The present invention relates to fungal strains capable of producing insecticide and a process for production of insecticide. It also relates to a method of cultivation of fungal strains and a fermentation medium for culturing the fungal strains.

20 Claims, 10 Drawing Sheets

US 8,497,090 B2

FUNGAL STRAINS AND A PROCESS FOR PRODUCTION OF INSECTICIDE THEREOF

CROSS-REFERENCE TO RELATED APPLICATIONS

Figure 1:
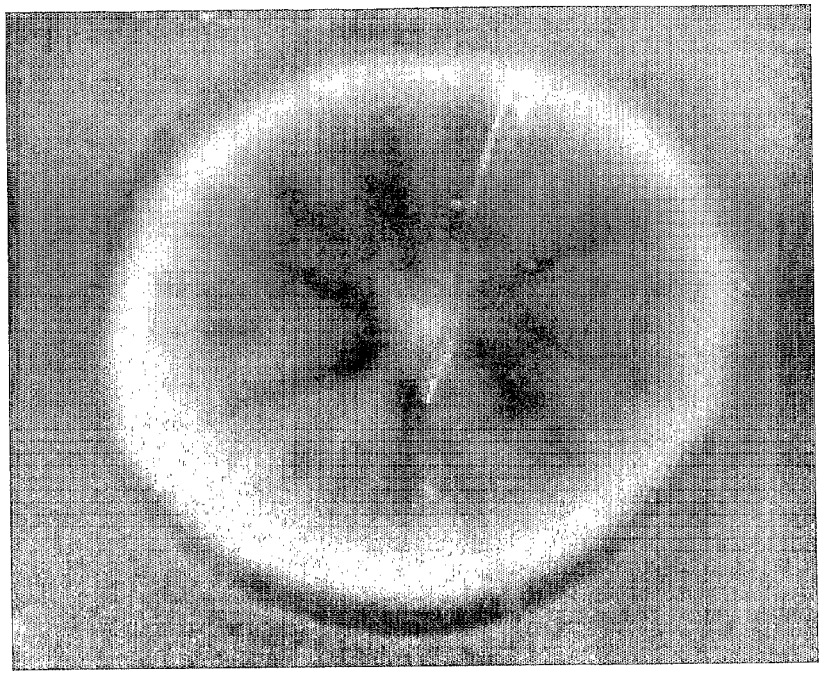
Figure 1:
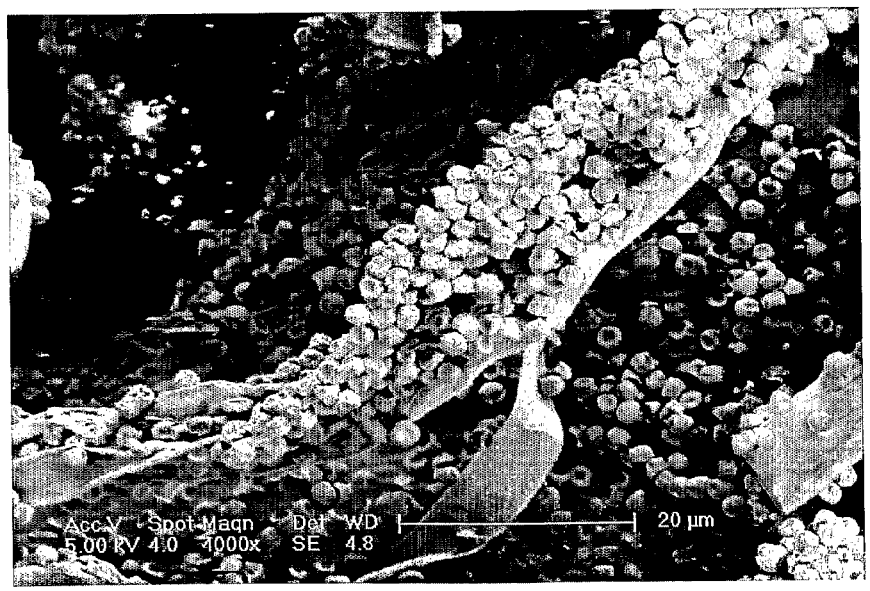

This application is a national stage application of International Application No. PCT/IN2008/000697, filed Oct. 2, 2008, whose benefit is claimed and which claims the benefit of Indian Patent Application No. 02392/CHE/2007, filed Oct. 23, 2007, the entire disclosures of which are incorporated herein by reference.

FIELD OF THE INVENTION

The present invention relates to fungal strains producing insecticide, a process for the production of insecticide spinosyns and biologically pure culture of fungal strains for use in the process. The invention relates to isolation of novel strains of fungi having deposition number IISBC35, IISBC28, IISBC19, IISBC12 and IISBC07 and the process for producing insecticide using these strains.

BACKGROUND OF THE INVENTION AND PRIOR ART

The spinosyns are a novel family of fermentation-derived natural products that exhibit potent insecticidal activities. Spinosad, a naturally-occurring mixture of spinosyn A and spinosyn D, is derived from a soil actinomycete bacterium species, *Saccharopolyspora spinosa* (Mertz and Yao 1990) and has successfully established its utility for crop protective applications in the agrochemical field in many countries including India. Recently, a new class of spinosyn was discovered from *S. pogona* NRRL 30141 (Hahn et al., 2006). The butenyl-spinosyns, also called pogonins, are very similar to spinosyns, differing in the length of the side chain at C-21 and in the variety of novel minor factors.

Fermentation development studies showed that for high spinosyn production, pH control and slow use of the carbon source was essential. Although, production of various insecticides by culturing different microorganism is known, there are a number of problems associated with these processes. Most of them describe batch fermentation processes where the nutrients are added or mixed in with the microorganism in the culture medium at the beginning of the production process. Generally, (the fixed amount of) these nutrients are therefore gradually used up during fermentation. However, at the beginning of the process, because the nutrients are at relatively high concentrations, production of desired compound is low because the microorganisms use carbon and nitrogen sources to grow, rather than to produce the drug. In such a process, the rate of production of the desired product is largely uncontrollable. Overall production levels are low because in the batch processes nutrients are in effect supplied only once to the microorganism and so no variation (at least during production) can be conducted to balance growth of the biomass with production of the fermentation product.

Till date the best producers of spinosyns are different strains of *Saccharopolyspora spinosa*. However, *Saccharopolyspora spinosa* requires extensive fermentation duration for spinosyn formation in the culture broth and purification procedures (U.S. Pat. No. 5,362,634).

The present disclosure overcomes the limitations associated in the prior art mentioned above.

OBJECTS OF THE INVENTION

The main object of the present invention is to obtain fungal strains capable of producing insecticide.

Another object of the present invention is to obtain strains having accession numbers 5394, 5393, 5392, 5391 and 5390 deposited at MTCC, Chandigarh.

Yet another object of the present invention is to obtain a biologically pure culture of fungal strains capable of producing insecticide.

Still another object of the present invention is to develop a process for production of insecticide from the fungal strains.

Still another object of the present invention is to develop a process for production of spinosyn from the fungal strains.

Still another object of the present invention is to develop a method of cultivation of fungal strains capable of producing insecticide.

Still another object of the present invention is to obtain a fermentation medium for culturing the fungal strains capable of producing insecticide.

STATEMENT OF THE INVENTION

Accordingly, the present invention relates to fungal strains capable of producing insecticide, said strains having accession numbers 5394, 5393, 5392, 5391 and 5390 deposited at MTCC, Chandigarh; a biologically pure culture of fungal strains capable of producing insecticide, said strains having accession numbers 5394, 5393, 5392, 5391 and 5390 deposited at MTCC, Chandigarh; a process for production of insecticide from the fungal strains having accession numbers 5394, 5393, 5392, 5391 and 5390 deposited at MTCC, Chandigarh, said process comprises step of culturing the fungal strains; a method of cultivation of fungal strains capable of producing insecticide, said strains having accession numbers 5394, 5393, 5392, 5391 and 5390 deposited at MTCC, Chandigarh, wherein the method comprises step of culturing said strains in a static, submerged condition at a temperature ranging from about 25° C. to about 35° C. and pH ranging from about 3 to about 8 for a period ranging from about 2 to about 8 days; and a fermentation medium for culturing the fungal strains capable of producing insecticide, said strains having accession numbers 5394, 5393, 5392, 5391 and 5390 deposited at MTCC, Chandigarh, wherein the medium comprises carbon source at a concentration ranging from about 1% w/v to about 10% w/v, nitrogen source at a concentration ranging from about 0.1% w/v to about 4% w/v, phosphate source at a concentration ranging from about 0.01% w/v to about 1% w/v and microelements.

BRIEF DESCRIPTION OF ACCOMPANYING DRAWINGS

FIG. 1: shows a view of *Aspergillus terreus* strain IISBC35 MTCC 5394 grown on potato dextrose medium and scanning electron microscopy (SEM) view of mycelium and spores.

Figure 2:
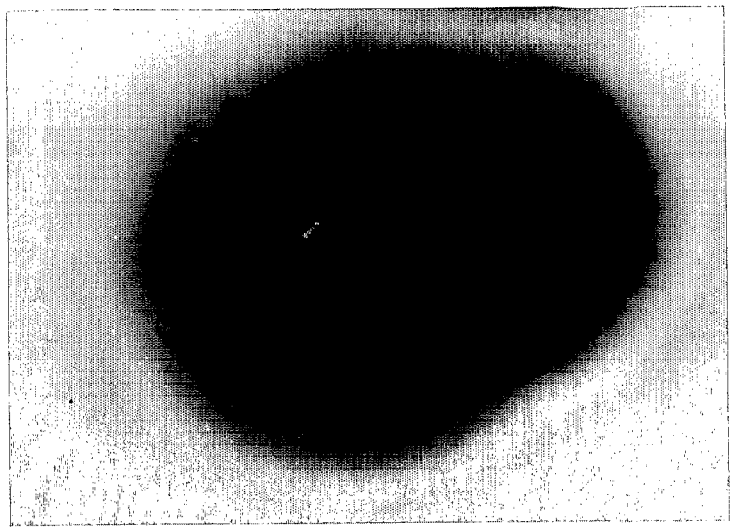
Figure 2:
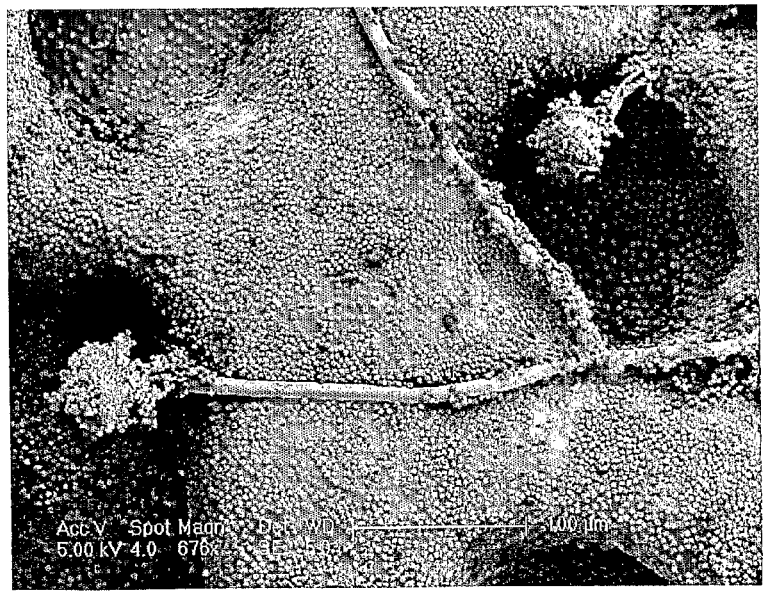

FIG. 2: shows a view of *Aspergillus niger* strain IISBC28 MTCC 5393 grown on potato dextrose medium and scanning electron microscopy (SEM) view of mycelium and spores.

Figure 3:
Figure 3:
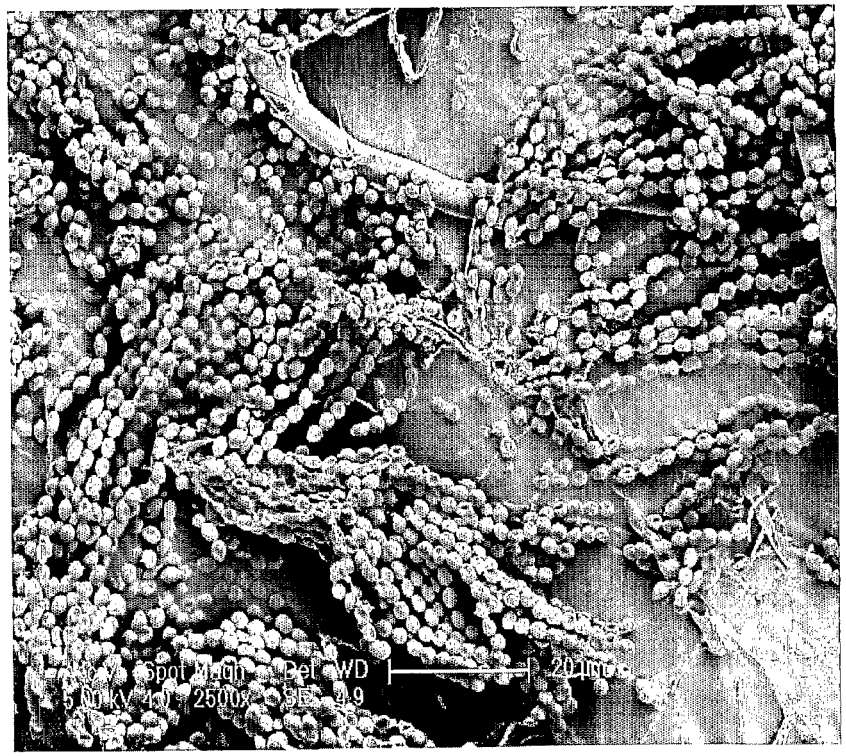

FIG. 3: shows a view of *Aspergillus glaucus* strain IISBC19 MTCC 5392 grown on potato dextrose medium and scanning electron microscopy (SEM) view of mycelium and spores.

Figure 4:
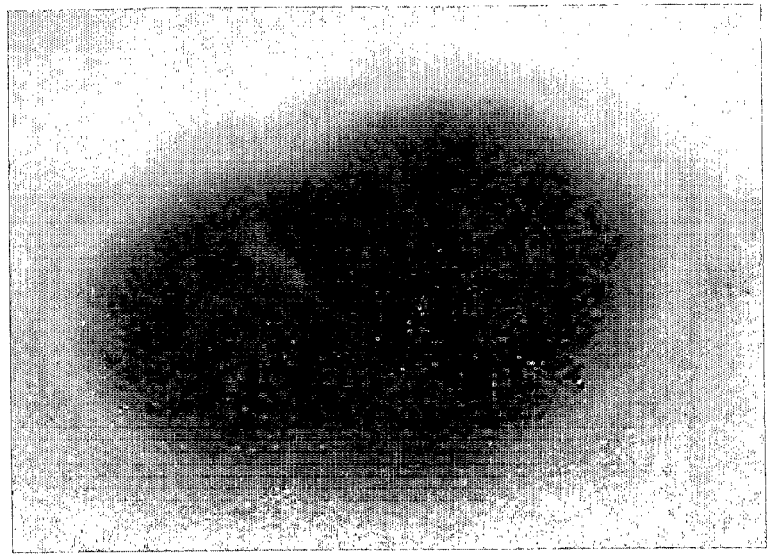
Figure 4:
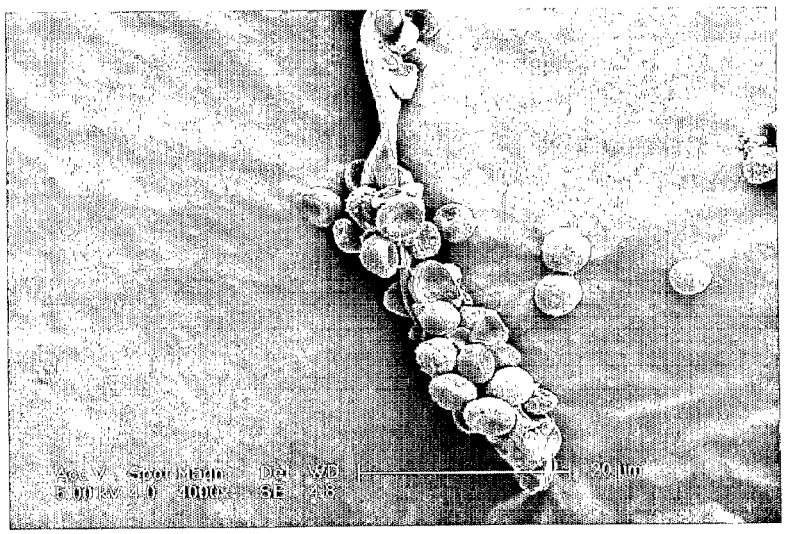

FIG. 4: shows a view of *Aspergillus wentii* strain IISBC12 MTCC 5391 grown on potato dextrose medium and scanning electron microscopy (SEM) view of mycelium and spores.

Figure 5:
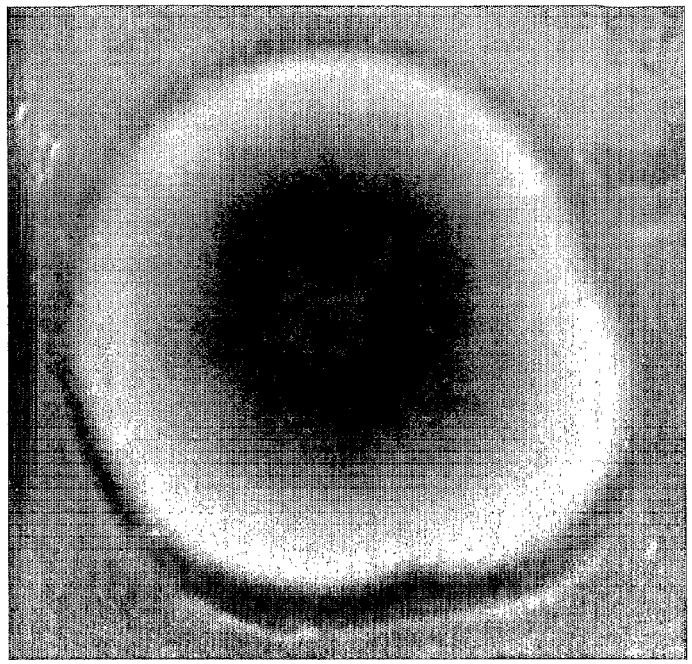
Figure 5:
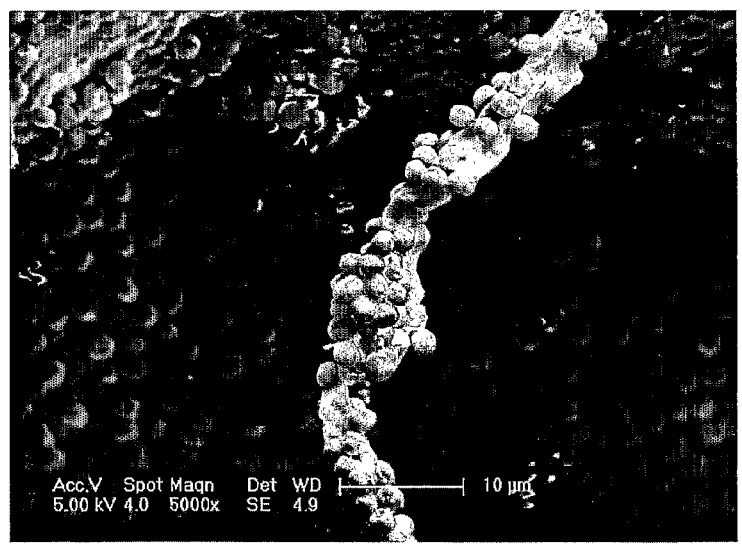

FIG. 5: shows a view of *Aspergillus terreus* strain IISBC07 MTCC 5390 grown on potato dextrose medium and scanning electron microscopy (SEM) view of mycelium and spores.

Figure 6:
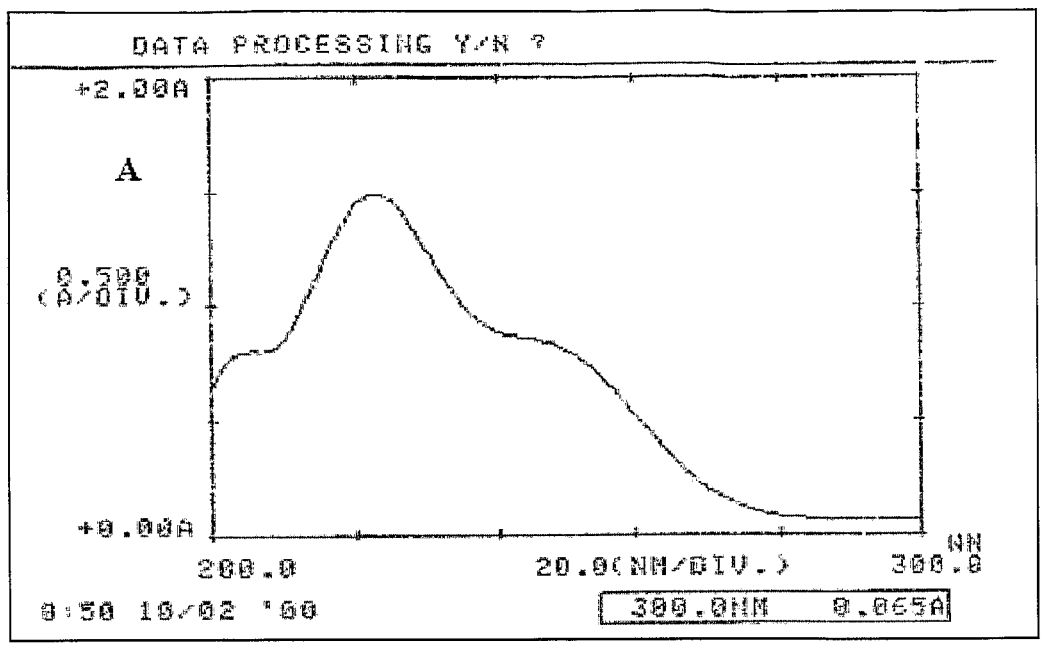
Figure 6:
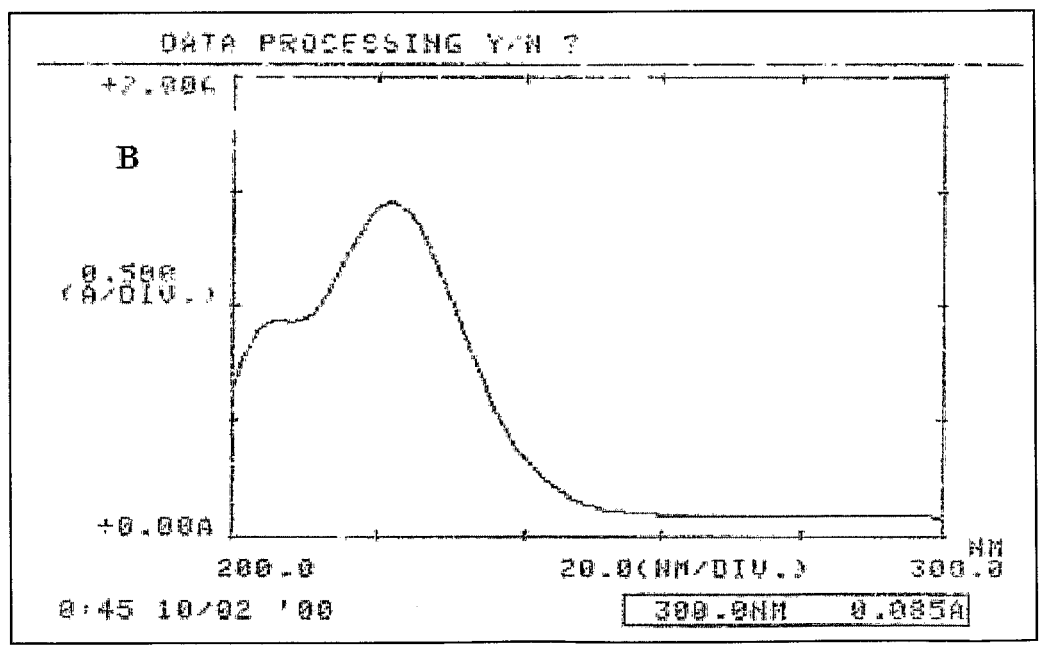

FIG. 6: Ultra Violet spectrum of the standard spinosyn (A) and compound obtained (B) from *Aspergillus terreus* strain IISBC35.

Figure 7:
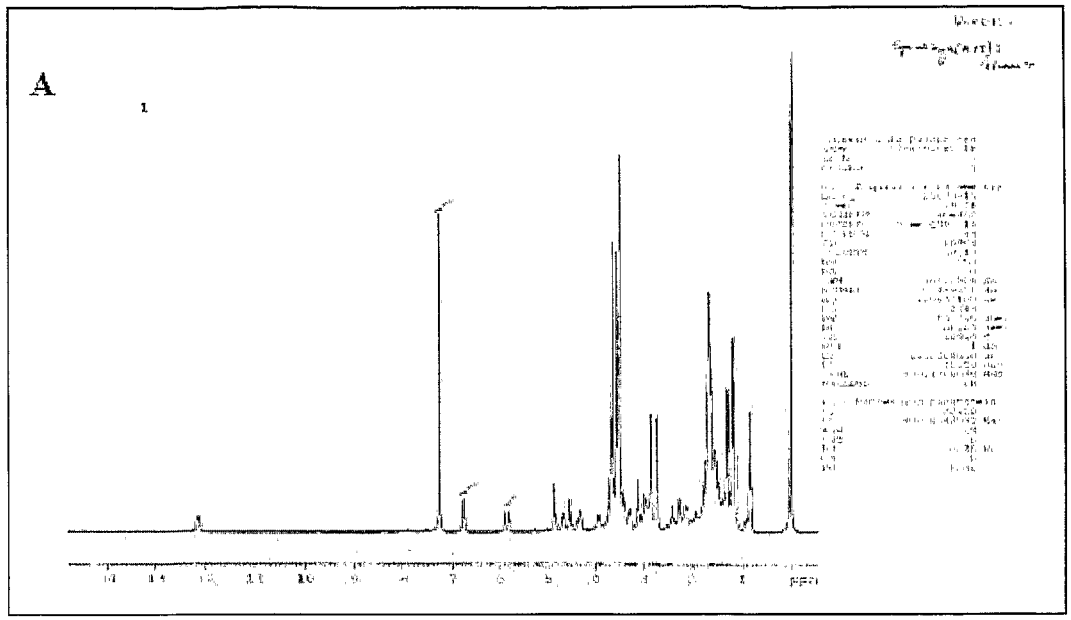
Figure 7:
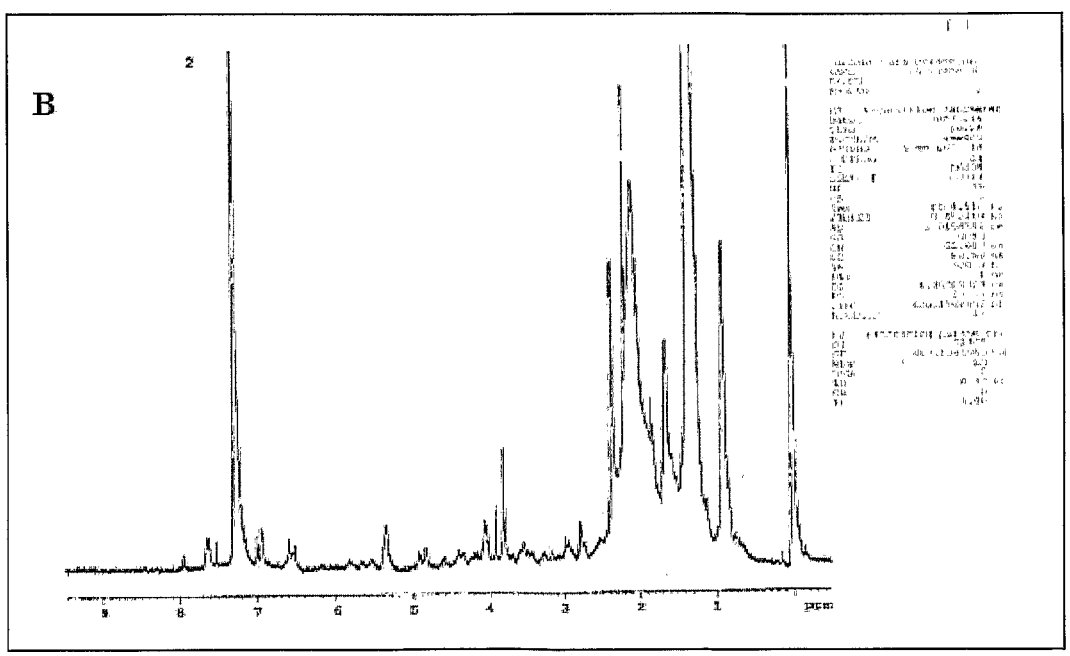

FIG. 7: Proton Nuclear Magnetic Resonance spectrum of the standard spinosyn (A) and compound (B) obtained from *Aspergillus terreus* strain IISBC35.

Figure 8:
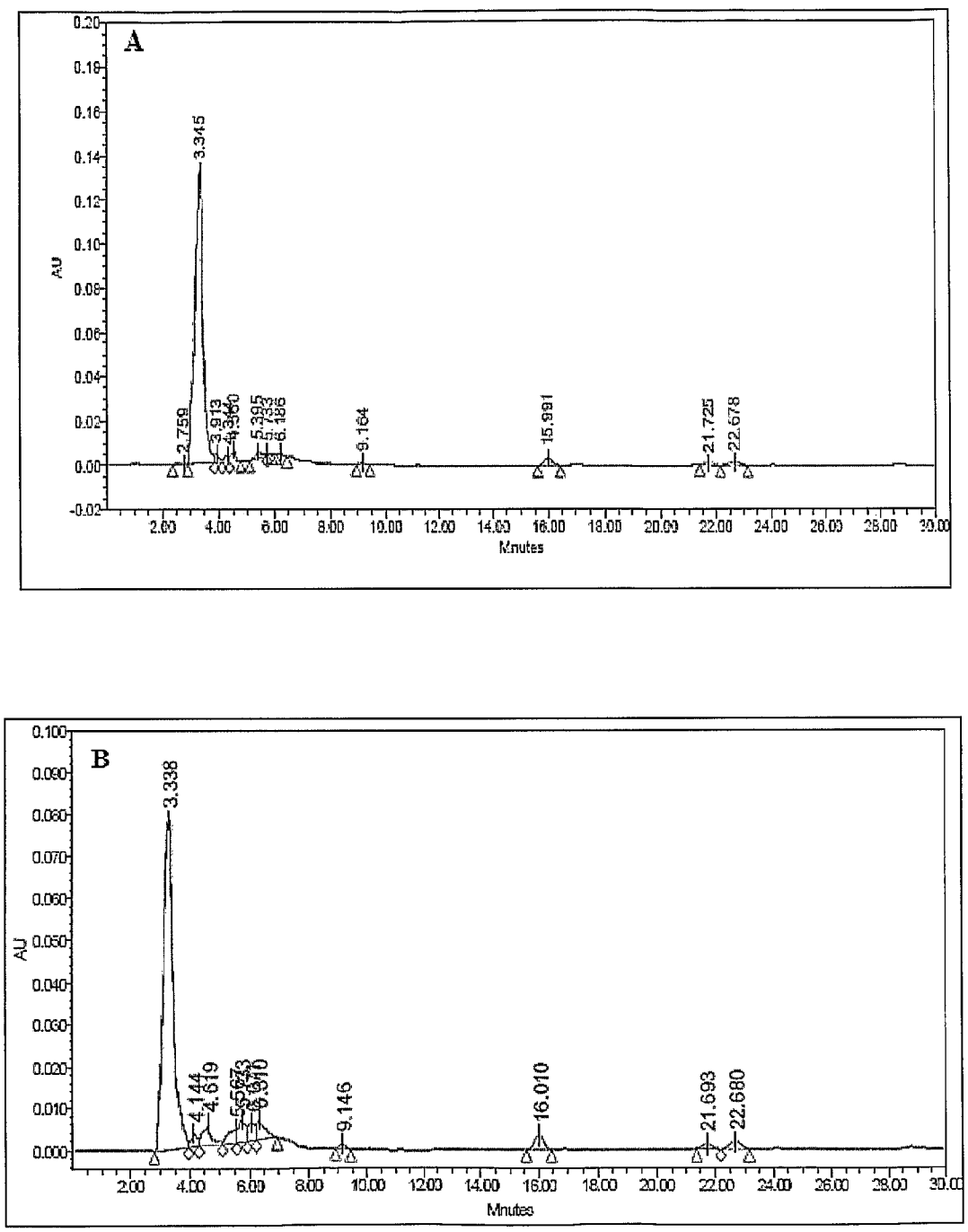

FIG. 8: HPLC analysis of standard spinosyn (A) and biomass extract (B) of *Aspergillus terreus* strain IISBC35 produced according to the experiments described in the invention.

Figure 9:
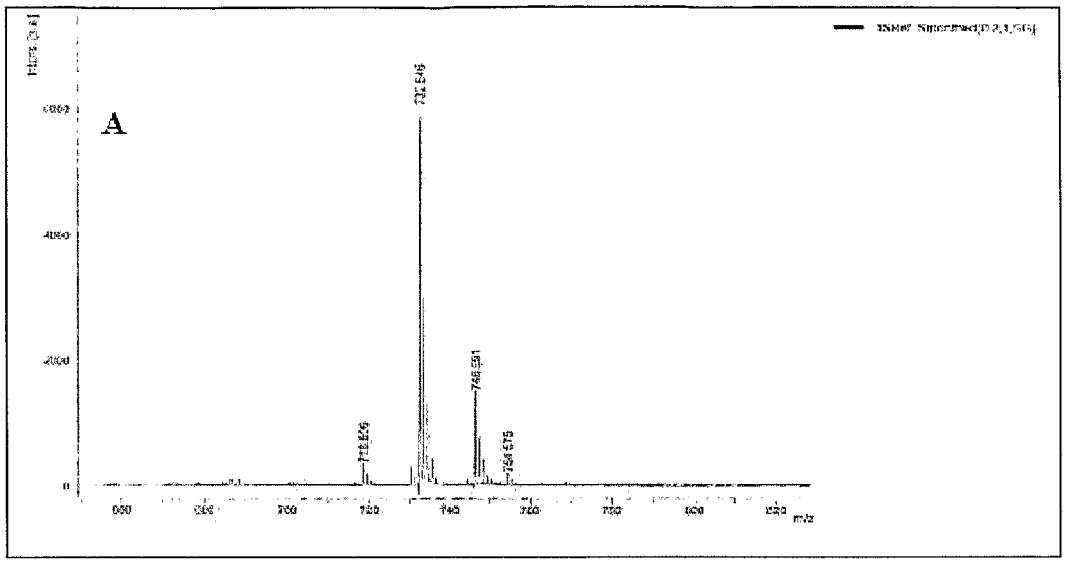
Figure 9:
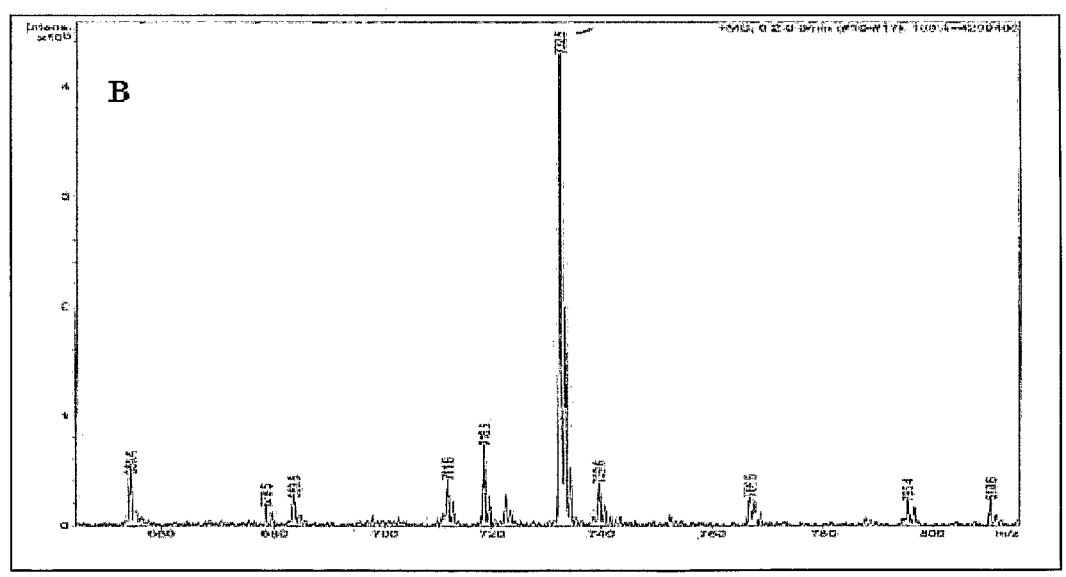

FIG. 9: Mass Spectrum of the standard spinosyn (A) and compound (B) obtained from *Aspergillus terreus* strain IISBC35.

Figure 10:
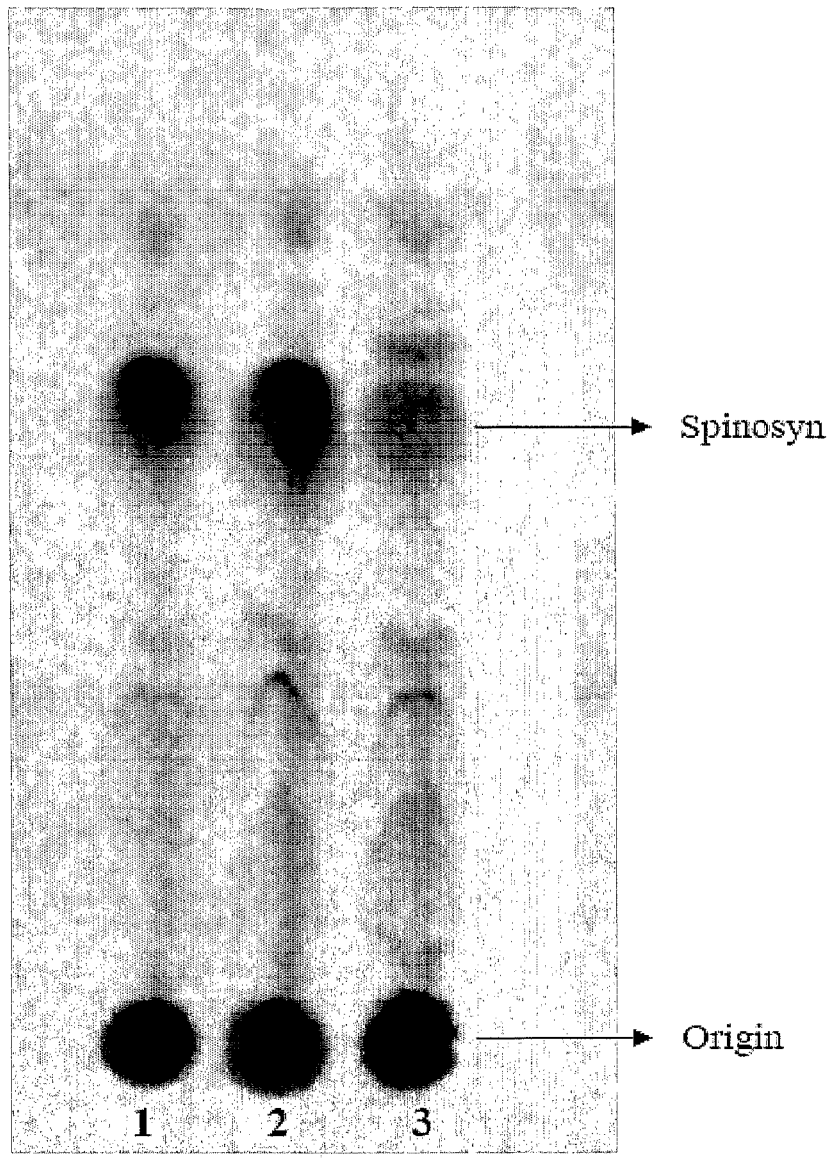

FIG. 10: Silica TLC plate after phosphor imaging showing the sequential appearance of spinosyn formation (Lane 1: Extract of 120 hr grown fungal biomass, Lane 2: Extract of 144 hr grown fungal biomass, Lane 3: Extract of 168 hr grown fungal biomass).

DETAILED DESCRIPTION OF THE INVENTION

The present invention relates to fungal strains capable of producing insecticide, said strains having accession numbers 5394, 5393, 5392, 5391 and 5390, all of which were deposited on Dec. 26, 2007 at Microbial Type Culture Collection & Gene Bank Institute of Microbial Technology, located at Sector 39- A. Chandigarh-160 036, India ("MTCC, Chandigarh").

In another embodiment of the present invention, the strains belong to genus *Aspergillus*.

In yet another embodiment of the present invention, the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07.

In still another embodiment of the present invention, the insecticide is spinosyn.

The present invention relates to a biologically pure culture of fungal strains capable of producing insecticide, said strains having accession numbers 5394, 5393, 5392, 5391 and 5390 deposited at MTCC, Chandigarh.

In still another embodiment of the present invention, the strains belong to genus *Aspergillus*.

In still another embodiment of the present invention, the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07.

In still another embodiment of the present invention, the insecticide is spinosyn.

The present invention relates to a process for production of insecticide from the fungal strains having accession numbers 5394, 5393, 5392, 5391 and 5390 deposited at MTCC, Chandigarh, said process comprises step of culturing the fungal strains.

In still another embodiment of the present invention, the fungal strains belong to genus *Aspergillus*.

In still another embodiment of the present invention, the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07.

In still another embodiment of the present invention, the insecticide is spinosyn In still another embodiment of the present invention, the fungal strains are cultured in a fermentation medium to obtain biomass.

In still another embodiment of the present invention, the biomass is dried and extracted with an organic solvent in ratio of about 1:5 to about 1:20, preferably about 1:10.

In still another embodiment of the present invention, the extraction with organic solvent is followed by constant shaking for 15 to 60 minutes.

In still another embodiment of the present invention, the organic solvent is selected from a group comprising methanol, ethyl acetate, acetonitrile, chloroform, dichloromethane and combinations thereof, preferably methanol.

In still another embodiment of the present invention, the extracted biomass is filtered followed by concentration at a temperature ranging from about 30° C. to about 45° C. to obtain the insecticide.

The present invention relates to a method of cultivation of fungal strains capable of producing insecticide, said strains having accession numbers 5394, 5393, 5392, 5391 and 5390 deposited at MTCC, Chandigarh, wherein the method comprises step of culturing said strains in a static, submerged condition at a temperature ranging from about 25° C. to about 35° C. and pH ranging from about 3 to about 8 for a period ranging from about 2 to about 8 days.

In still another embodiment of the present invention, the temperature is preferably about 30° C. and the pH is preferably about 4.5.

In still another embodiment of the present invention, the strains are cultured for a period preferably of about 6 days.

The present invention relates to a fermentation medium for culturing the fungal strains capable of producing insecticide, said strains having accession numbers 5394, 5393, 5392, 5391 and 5390 deposited at MTCC, Chandigarh, wherein the medium comprises carbon source at a concentration ranging from about 1% w/v to about 10% w/v, nitrogen source at a concentration ranging from about 0.1% w/v to about 4% w/v, phosphate source at a concentration ranging from about 0.01% w/v to about 1% w/v and microelements.

In still another embodiment of the present invention, the carbon source is at a concentration preferably about 6% w/v, nitrogen source is at a concentration preferably about 1% w/v and phosphate source is at a concentration preferably about 0.1% w/v.

In still another embodiment of the present invention, the carbon source is saccharide(s) selected from a group comprising glucose, sucrose and combination thereof.

In still another embodiment of the present invention, the nitrogen source is selected from a group comprising yeast hydrolysates or extract, bacteriological peptone, soya peptone and corn steep liquor and combinations thereof, preferably soya peptone.

In still another embodiment of the present invention, the phosphate source is selected from a group comprising dipotassium hydrogen phosphate, potassium dihydrogen phosphate and combination thereof.

In still another embodiment of the present invention, the microelements are selected from a group comprising iron, manganese, zinc, copper, sodium and combinations thereof.

In still another embodiment of the present invention, the iron is at a concentration ranging from about 50-200 mg/L, preferably 100 mg/L, manganese at a concentration ranging from about 1-10 mg/L, preferably 5 mg/L, zinc at a concentration ranging from about 100-1000 mg/L, preferably 500 mg/L, copper at a concentration ranging from about 10-100 mg/L, preferably 25 mg/L and sodium at a concentration ranging from about 1-10 mg/L, preferably 5 mg/L.

The present invention is directed to a process for the preparation of spinosyns and biologically pure culture for use in the process. The disclosure relates to isolation of various microorganisms from soil in search of spinosyns produced by these microorganisms. The spinosyn-producing strains belong to the genus *Aspergillus* isolated from the soil at Karnataka, India. From its morphological and cultural properties described herein below, the strains were identified as *Aspergillus* species and deposited at MTCC, Chandigarh, India.

The process involves culturing a variety of fungal strains specifically *Aspergillus* groups to produce high yields of biologically active spinosyns. The spinosyn compounds are isolated by two-step processes and are formulated for the use as an active ingredient of insecticide for controlling ectoparasites. The fermentation process provides a greater degree of control and/or flexibility for over production, so that the manufacturer can vary conditions to optimize production of the desired fermentation product.

The genus *Aspergillus* especially *A. terreus* strain has been the subject of research and industrial use for several decades (Demain, 1983; 2006). Hence, *A. terreus* was considered as prolific producer of several beneficial secondary metabolites. A few of the compounds that are produced by *A. terreus* are aspulvinone (Takahashi et al., 1978), asterric acid (Curtis et al., 1960), asterriquinone (Kaji et al., 1994), butyrolactone I (Nitta et al., 1983), citrinin (Sankawa et al., 1983), emodin (Chen et al., 1992), geodin (Kiriyama et al., 1977), itaconate (Bonnarme et al., 1995), lovastatin (Greenspan and Yudkovitz, 1985), questrin (Curtis et al., 1960), sulochrin (Vinci et al., 1991), terrecyclic acid (Nakagawa et al., 1982), Terreulactones (Cho et al., 1993; Kim et al., 2002) and Isoterreulactone A (Yoo et al., 2005). Further, *A. terreus* is generally regarded as a safe organism. This is documented in lists of the organizations responsible for occupational health and safety (Berufsgenossenschaftder Chemischen Industrie, 1998).

The present invention relates to cultivation of the isolated fungal strains producing insecticide. These strains are deposited, at MTCC, Chandigarh, India, and these deposits were made on Dec. 26, 2007. The strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07. These strains are cultivated in submerged culture containing defined nutrient media under static conditions.

In one aspect, the invention provides a method of cultivating submerged cultures of one or more *Aspergillus* strains having the trait to produce one or more substances having spinosyn activity. The use of the nutrient media of the invention, comprising a saccharide (glucose and sucrose), an organic or mineral source of nitrogen and a variety of salts, is especially suited to enhance the production of spinosyns.

In another aspect, the invention provides a method to concentrate the spinosyn compound mainly in the mycelium thus enabling the simple separation of biomass from the fermentation broth, thereby requiring no further extraction, concentration, purification or complex separation procedures. The simple separation of the *Aspergillus* biomass from the culture broth of the present invention is followed by the drying of the final spinosyn product at 30 deg C. to 45 deg C.

In another aspect, invention provides novel processes for making spinosyns by fermentation using *Aspergillus terreus* strain IISBC35 having accession No.5394, *Aspergillus niger* strain IISBC28 having accession No.5393, *Aspergillus glaucus* strain IISBC19 having accession No.5392, *Aspergillus wentii* strain IISBC12 having accession No.5391 and *Aspergillus terreus* strain IISBC07 strains having accession No 5390 deposited at MTCC, chandigarh.

In another aspect, the invention overcomes the deficiencies of the state of the art and to provide: i) a process for producing spinosyn compounds in an efficient, fast and economic way, and ii) novel spinosyn-producing strains on account of its inertness, which renders it easy and safe to handle in the laboratory and in commercial scale fermentations.

A process according to the invention comprises the submerged cultivation of Ascomycetes fungi, producers of spinosyns, belonging to the genus *Aspergillus* on a nutrient media including nitrogen, mineral salts and a source of carbon- mono- or disaccharides including glucose; one-step isolation procedure from a fermentation broth obtained from the submerged culture under static conditions.

The spinosyns are a family of potent and highly selective insect control agents that display a favorable environmental profile. The spinosyn, natural insecticide derived from an actinomycete bacterium species, *Saccharopolyspora spinosa* (Mertz and Yao 1990), displays the efficacy of a synthetic insecticide. It consists of the two most active metabolites, designated spinosyn A and D. Both spinosyns are readily degraded in moist aerobic soil, and field dissipation. Spinosad causes neurological effects in insects that are consistent with the general activation of nicotinic acetylcholine receptors. Spinosad has a high level of efficacy for lepidopteran larvae, as well as some Diptera, Coleoptera, Thysanoptera and Hymenoptera, but has limited to no activity to other insects and exhibits low toxicity to mammals and other wildlife.

A process for extraction of spinosyns from the biomass obtained from the cultures of *Aspergillus terreus* strain IISBC35 having accession No.5394, *Aspergillus niger* strain IISBC28 having accession No.5393, *Aspergillus glaucus* strain IISBC19 having accession No.5392, *Aspergillus wentii* strain IISBC12 having accession No.5391 and *Aspergillus terreus* strain IISBC07 strains having accession No 5390 deposited at MTCC, chandigarh was extracted with methanol. The fungal mycelium obtained after 6 days of incubation was filtered and dried in between folds of sterilized bottling paper. The dried biomass obtained was extracted with methanol in the ratio of 1:10 and kept for constant shaking for 30 min. The extracted biomass was filtered to remove debris and concentrated in vacuum drier at temperature range of 30 deg C. to 45 deg C. The oily, viscous compound obtained was used for further characterization.

The general efficiency of processes for spinosyn production is determined by the productivity of fungal strains and the number of steps in the extraction procedure. The strains of *Aspergillus* used in the present invention were obtained from various soil samples from Karnataka, India. The morphological and cultural properties described herein below, the strains were identified as *Aspergillus* species, and deposited as *Aspergillus terreus* strain IISBC35 having accession No.5394, *Aspergillus niger* strain IISBC28 having accession No.5393, *Aspergillus glaucus* strain IISBC19 having accession No.5392, *Aspergillus wentii* strain IISBC12 having accession No.5391 and *Aspergillus terreus* strain IISBC07 having accession No.5390 at MTCC, chandigarh, India. The above described strains were grown to purity and maintained on potato dextrose agar medium.

The culture of these strains to produce spinosyn is carried out in aqueous media such as those employed for good mycelium growth and biomass accumulation. Such media contain sources of carbon, nitrogen and inorganic salts assimilated by the growing culture. All species of genus *Aspergillus* are capable of utilizing monosaccharide and disaccharides that are good sources of carbon for their growth. Glucose and sucrose are the main ingredients that were used either alone or in combination as sources of carbon. The amount of carbohydrate usually varies between about 1.5% and 6% by weight of the medium to provide a high yield of biomass.

The best sources of nitrogen possessing it in organic form include yeast hydrolysates or extract, bacteriological peptone, soya peptone, corn steep liquor and the like. The sources of nitrogen either alone or in combination are used in the range of 0.1% to 2% by weight of the medium to provide a high yield of biomass.

The best phosphate sources to be incorporated in the culture media is in the form of di-potassium hydrogen phosphate ($K_2HPO_4$) or potassium di-hydrogen phosphate ($KH_2PO_4$) are needed for the fungal growth. Further, the main microelements Fe, Mn, Zn Cu and Na are available from any type of inorganic salts to obtain the enhanced fungal biomass formation in the static submerged fermentation process for spinosyn production. The concentration ranges of micro elements used in the fermentation medium are as follows:

| | |
|---|---|
| $Zn^{2+}$ | 100-1000 mg/L, preferably 500 mg/L |
| $Fe^{2+}$ | 50-200 mg/L, preferably 100 mg/L |
| $Cu^{2+}$ | 10-100 mg/L, preferably 25 mg/L |
| $Mn^{2+}$ | 1-10 mg/L, preferably 5 mg/L |
| $Na^{2+}$ | 1-10 mg/L, preferably 5 mg/L |

The fermentation is carried out at temperatures ranging from 28 deg C. to 35 deg C. for a period of 6 days. The optimal temperature for growth is 30 deg C.; further increase of temperature beyond 35 deg C. is detrimental for fungal biomass formation.

Strobel et al., (1993) have reported 35 μg/ml of spinosyns from wild strain of *Saccharopolyspora spinosa* A83543.3 under submerged conditions in 7 days of fermentation duration. Zhi-hua et al., (2006) have also noticed similar kind of observation from wild strain of *Saccharopolyspora spinosa* yielding 121 μg/ml of spinosyns in cultivation period of 7 days. However, from our studies, the yield is 149 μg/ml of spinosyn from *Aspergillus terreus* IISBC 35 strain from 6-days of fermentation duration.

The yield from the strains of instant disclosure is as provided below in ng/ml:

| Strains | Yield of spinosyn (ng/ml) |
|---|---|
| *Aspergillus terreus* IISBC07 (Accession No. 5390) | 1.122 |
| *Aspergillus wentii* IISBC12 (Accession No. 5391) | 0.798 |
| *Aspergillus glaucus* IISBC19 (Accession No. 5392) | 0.819 |
| *Aspergillus niger* IISBC28 (Accession No. 5393) | 0.621 |
| *Aspergillus terreus* IISBC35 (Accession No. 5394) | 1.985 |

Characterization of Novel Strains Obtained in the Instant Invention:

*Aspergillus terreus* IISBC07: It has cinnamon brown, circular colonies with long, compactly columnar conidial heads having hyaline mycelium.

*Aspergillus wentii* IISBC12: It has plane grayish yellow, plane or lightly wrinkled colonies and conidiophores are densely packed on the surface.

*Aspergillus glaucus* IISBC19: It has deep/tan green spreading colonies and conidiophores are loosely packed on the surface.

*Aspergillus niger* IISBC28: It has black colored colony with pale yellow spreading, circular margins. The conidiophores are loosely packed with black colored conidia.

*Aspergillus terreus* IISBC35: It has cinnamon brown or sand colored, circular colonies with long, compactly columnar conidial heads having hyaline mycelium with undulating texture on the surface.

The basic microscopic morphology is same for all the species of *Aspergillus*. However, microscopic structures are unique to certain species and constitute the key features for species identification together with the surface color of the colony. The common microscopic features of most of the *Aspergillus* species include septate and hyaline hyphae. The conidiophores originate from the basal foot cell located on the supporting hyphae and terminate in a vesicle at the apex. The vesicle formation in the mentioned fungus is the typical diagnostic character of *Aspergillus* genus.

Macroscopic features including of both surface and reverse, colony characters of few *Aspergillus* species are as mentioned below:

| Species | Surface | Reverse |
|---|---|---|
| *A. terreus* | Cinnamon to brown | White to brown |
| *A. niger* | Black | White to yellow |
| *A. glaucus* | Green | Yellowish to brown |
| *A. wentii* | Green with yellow areas | Yellowish to brown |

The invention is further elaborated with the help of following examples. However, these examples should not be construed to limit the scope of the invention.

EXAMPLE 1

Source of Microorganisms

Soil samples from various regions of Karnataka (India) were used to isolate the fungal strains as per the method of Seifert, 1990 and identified as per Raper and Fennell (1965). The isolates were grown on the following media (FIG. 1-5) and the stock cultures were maintained at the Indian Institute of Science, Bangalore, India and also deposited in Microbial Type Culture Collection, Chandigarh, India and given an accession number *Aspergillus terreus* IISBC35 MTCC 5394, *Aspergillus niger* IISBC28 MTCC 5393, *Aspergillus glaucus* IISBC19 MTCC 5392, *Aspergillus wentii* IISBC12 MTCC 5391 and *Aspergillus terreus* IISBC07 MTCC 5390. The composition of various media used for the cultivation and maintenance of above fungal strains are as follows.

| Potato Dextrose Agar (PDA) | |
|---|---|
| Potato* | 200.0 g |
| Dextrose | 20.0 g |
| Agar | 15.0 g |
| Distilled water | 1 liter |

*Boiled diced potatoes in 500 ml of water until thoroughly cooked, filter through cheese cloth. Add dextrose to the filtrate and adjust the pH to 4.5 units. Dissolve agar in water and bring up the required volume by the addition of water. Autoclave the contents at 15 lb pressure for 15 minutes.

| Czapek - Dox Agar | |
| --- | --- |
| K2HPO4 | 1.0 g |
| NaNO3 | 3.0 g |
| KCl | 0.5 g |
| MgSO4•7H2O | 0.5 g |
| FeSO4•7H2O | 0.01 g |
| Sucrose | 30.0 g |
| Agar | 15.0 g |
| Distilled water | 1 liter |

Dissolve all the ingredients except phosphate in half of the water and sucrose was added. Adjust the pH to 6.3 units and make up the volume to 1 liter

| Sabouraud's Agar | |
| --- | --- |
| Peptone | 10.0 g |
| Dextrose | 40.0 g |
| Agar | 15.0 g |
| Distilled water | 1 liter |
| Adjust pH to | 5.6 |

EXAMPLE 2

Culturing of Fungal Strains on Liquid Medium

The insecticidal compound of the invention is synthesized in detectable quantities by growing the above strains mentioned in Example 1 on a suitable medium using standard surface culture methods. Suitable media include, but not limited to potato dextrose broth, Czapek-Dox broth and Vogel's spinosyn screening medium. Preferably the Vogel's spinosyn screening medium used for initial cultivation of fungal strains and the composition as follows. Spinosyn screening medium having the following composition was used Sucrose 15 g/L, Vogel's minimal medium 20 ml/L, distilled water 1000 mL. The pH of the medium was adjusted to 4.5 units. The sterile medium was transferred into 10 mL culture tubes and inoculated with 10 days old fungal spores. The inoculated test tubes were incubated at 30 deg C. for 6 days.

| Vogel's spinosyn screening medium | |
| --- | --- |
| Vogel's salts (50X)* | 20 ml |
| Sucrose | 15 g |
| Distilled water | 1 liter |
| pH | 4.5 Units |
| *Vogel's Salts (50X) | |
| Na3 Citrate | 150.0 g |
| KH$_2$PO$_4$ | 250.0 g |
| NH$_4$NO$_3$ | 100.0 g |
| MgSO$_4$•7H$_2$O | 10.0 g |
| CaCl$_2$•2H$_2$O | 5.0 g |
| Trace element solution[1] | 5.0 ml |
| Biotin solution[2] | 2.5 ml |
| Distilled water | 1 liter |
| Trace element solution[1] | |
| Citric acid | 5.0 g |
| ZnSO$_4$•7H$_2$O | 5.0 g |
| Fe (NH4)$_2$(SO4)$_2$•6H$_2$O | 1.0 g |
| CaSO$_4$•5H$_2$O | 0.25 g |
| MnSO$_4$•1H$_2$O | 0.05 g |
| H3BO$_3$, anhydrous | 0.05 g |

| Vogel's spinosyn screening medium | |
| --- | --- |
| Na$_2$MoO$_4$•2H$_2$O | 0.05 g |
| Distilled water | 100 ml |
| Biotin solution[2] | |
| Biotin | 5.0 mg |
| Distilled water | 50 ml |

EXAMPLE 3

Liquid Fermentation Process for Spinosyn Production

The insecticidal compound of the invention is mass produced by growing the fungal strains in Vogel's spinosyn production medium and the composition of same as follows.

| Vogel's spinosyn production medium | |
| --- | --- |
| Vogel's salts (50X) | 20.0 ml |
| Sucrose | 60.0 g |
| Soya peptone | 10.0 g |
| KH2PO4 | 1.0 g |
| Distilled water | 1 liter |
| pH | 4.5 units |

The fermentation is in a manner that the biomass in the culture flask substantially comprises at least of about 80% filamentous mycelium. This can be achieved by supplying an excess of carbon, limited nitrogen and phosphate source. The composition of the production medium can be varied over a wide range and the strains are cultivated using standard surface static culture methods.

A culture tube with a 8-10 days old pure culture of *Aspergillus terreus* IISBC35 MTCC 5394, *Aspergillus niger* IISBC28 MTCC 5393, *Aspergillus glaucus* IISBC19 MTCC 5392, *Aspergillus wentii* IISBC12 MTCC 5391 and *Aspergillus terreus* IISBC07 MTCC 5390 were used for inoculation into production medium in an Erlenmeyer flask. The pH of the spinosyn production medium was adjusted to 4.5 units, which is necessary in order to achieve better mycelium formation. The contents of the inoculated medium were incubated at static conditions without agitation for 6 days at 30 deg C. The end of the fermentation can be easily determined by the standard method of biomass determination (e.g. dry mass determination). The 144-hour cultivation typically is sufficient to yield 30 grams per liter of dry mycelium.

The separation of the filamentous mycelium from the fermentation media is accomplished by standard procedures such as filtration, centrifugation or convenient means of separation. To avoid contaminating the mycelium with undesirable microorganisms, the mycelium is harvested under sterile conditions.

EXAMPLE 4

Extraction of Spinosyns and Assay

The fungal mycelium obtained after 6 days of incubation was filtered and dried in between folds of sterilized blotting paper. The dried biomass obtained was extracted with methanol in the ratio of 1:10 and kept at constant shaking for 30 min. The extracted biomass was filtered to remove debris and concentrated in vacuum drier at the temperature range of 30 deg C. to 45 deg C. The oily, viscous compound obtained was used for spinosyn assay using rapid assay kit.

Other than methanol, solvents comprising ethyl acetate, acetonitrile, chloroform, dichloromethane and their combinations are also used for extraction.

EXAMPLE 5

Preparation of Standard Spinosyns

The stock solution was prepared by dissolving 1 mL of Tracer® in 10 mL of methanol solution. The filtered solution was concentrated to dryness. The brown crystals of spinosyns obtained were used for the preparation of standard graph and for thin layer chromatography estimations.

EXAMPLE 6

Rapid Confirmation of Spinosyn Producing Isolates by Thin Layer Chromatography (TLC) Method The spinosyn positive isolates obtained through rapid assay kit were further confirmed through TLC method using standard spinosyn, a positive control. Crude spinosyn extracts from different isolates were loaded on silica gel plate and subjected to TLC. The spinosyns were separated using dichloromethane, chloroform and methanol (7:2:1) as solvent system. The spots on TLC plates (FIG. 10) were visualized by developing in an iodine chamber and the $R_f$ values were calculated. The crude fungal spinosyn revealed $R_f$ value of 0.49 which is identical to standard spinosyn on TLC plates.

EXAMPLE 7

Determination of Spinosyn by Ultra Violet Analysis

After the determination of $R_f$ values (of both standard and experimental samples), the area of the separated compounds were scrapped off and eluted with methanol and water (8:2). Thus, the desired product was recovered relatively in a pure form. The λ max of the above samples was recorded in UV spectrophotometer (FIG. 6) (Optima, Japan). The λ max of above samples was determined from 200-300 nm. The absorption maximum of both crude fungal extract and standard spinosyn was noticed at 222 nm. Further, the optical densities of samples were taken and the amount of spinosyn was calculated by referring the standard graph.

EXAMPLE 8

Analysis of Spinosyns Using High Performance Liquid Chromatography (HPLC)

Attempts were also made to confirm the spinosyns obtained from fungal biomass (TLC purified extract) through HPLC method. The biomass obtained after fermentation process was washed with water and extracted with methanol and filtered through 0.45 μm filter. 10 mL of organic phase was dried under vacuum at 45 deg C. The dried residues were dissolved with methanol and water (8:2). HPLC was carried out using $C_{18}$ reverse phase column (Strobel et al., 1993) thermostated at 30 deg C. The column was developed at a flow rate of 0.5 mL/min for 30 min with acetonitrile and water (60:40). The chromatograms were monitored at 222 nm and later identified by their retention time (FIG. 8). The spinosyns extracted from Tracer® was used as reference standard in the analysis. The result shows that the standard spinosyn elutes at the retention time of 3.3 minutes and the same is true with fungal extract confirming the occurrence of spinosyn molecule.

EXAMPLE 9

Proton Nuclear Magnetic Resonance ($^1$H NMR) for Spinosyn Analysis

The proton NMR spectra for both reference and synthesized spinosyns were recorded on JEOL model GSX 270 MHz (FIG. 7). The proton NMR spectra of both the samples revealed the presence of characteristic peaks at 3.8, 5.6 and 6.8 ppm indicating existence of spinosyn from fungal isolate.

EXAMPLE 10

Determination of Spinosyns Through Matrix-Assisted Laser Desorption Ionization (MALDI)-Electrospray Ionization (ESI) Mass Spectrometric Analysis HPLC purified spinosyns samples were subjected to MALDI-ESI analysis. MALDI mass spectrometric analysis was performed on a Kratos PC Kompact Seq 1.2.2 mass spectrometer in the linear mode. The mass obtained in these experiments was compared with the authentic spinosyn (FIG. 9). The mass analysis results revealed standard spinosyn has a peak at 732.54 (m/z+) which corresponds to spinosyn A molecule and the fungal extract has also identical peak at 732.5 (m/z+), confirming the occurrence of the spinosyn.

EXAMPLE 11

Detection of Acetate Dependent Metabolites in *Aspergillus terreus* IISBC35 by Pulse Labeling An attempt has been made to detect the acetate-dependent intermediary metabolites of *Aspergillus terreus* IISBC35 that are putative precursors of spinosyns using [$^{14}$C] acetate. The fungal colony was allowed to metabolize [$^{14}$C] acetate over various time intervals. The biosynthetic reactions were quenched by quick-freezing and the cells were disrupted & extracted with methanol. Silica thin layer chromatographic plates were then used to separate radioactive metabolites present. Autoradiography of the thin-layer chromatographic plates indicates the appearance of various intermediates, implicating the possible route of spinosyn biosynthesis in *Aspergillus terreus* IISBC35.

Biologically pure colony of *Aspergillus terreus* IISBC35 was inoculated into 10 ml of Vogel's medium and incubated at standard condition as described under earlier sections. The radiolabeled sodium acetate [$^{14}$CH$_3$$^{14}$CO$_2$Na] having specific activity (45.0 mCi/mmol) was employed in all of the experiment. After 4$^{th}$ day of inoculation radiolabeled precursor, sodium acetate (0.5 μCi/tube) was added aseptically in the culture medium. At chosen time points, the biosynthetic reaction was quenched by freezing. The extraction of metabolites was done for frozen biomass using methanol and separated on silica thin layer chromatography using chloroform-dichloromethane-methanol (7:2:1) solvent system. The identification of spinosyns was done using unlabeled authentic compound to determine the coincidence of migration position on silica-TLC plate. The spots on silica-TLC were visualized by phosphor imaging. The results revealed that the acetate acts as a precursor for biosynthesis of spinosyn and $R_f$ values obtained were comparable with results of Example 6. Further, the above method can be used as a powerful tool for [$^{14}$C] labeling of spinosyn molecule.

References

1) Boeck L D, Chio H, Eaton T E, Godfrey O W, Michel K H, Nakatsukasa W M and Yao R C, U.S. Pat. No. 5,362,634.
2) Bonnarme P, Gillet B, Sepulchre A M, Role C, Beloeil J C and Ducrocq C. J. Bacteriol. 1995: 177:3573-3578.
3) Berufsgenossenschaft der Chemischen Industrie (1998) Merkblatt B 007. Jedermann, Heidelberg.
4) Curtis R F, Hassall C H, Jones D W and Williams T W. J. Chem. Soc. 1960: 4836-4842
5) Chen Z G, Fujii I, Ebizuka Y and Sankawa U. Arch. Microbiol. 1992: 158:29-34.
6) Cho K M, Kim W G, Lee C K and Yoo I D. J Antibiot (Tokyo). 2003 April; 56(4):344-50.
7) Demain A L. Biochem Soc Symp. 1983; 48:117-32.
8) Demain A L. J Ind Microbiol Biotechnol 33:486-495
9) Greenspan M D and Yudkovitz J B. J. Bacteriol. 1985: 162:704-707.
10) Hahn D R, Gustafson G, Waldron C, Bullard B, Jackson J D and Mitchell J. J Ind Microbiol Biotechnol. 2006 February; 33(2):94-104. Epub 2005 Sep. 23.
11) Kaji A, Iwata T, Kiriyama N, Wakusawa S and Miyamoto K. Chem. Pharm. Bull. (Tokyo) 1994: 42:1682-1684.
12) Kim W G, Cho K M, Lee C K and Yoo I D. Tetrahedron Lett. Pergamon 2002: 43:3197-3198
13) Kiriyama N, Nitta K, Sakaguchi Y, Tagushi Y and Yamamoto Y. Chem. Pharm. Bull. (Tokyo) 1977: 25:2593-2601.
14) Mertz and Yao, International J Systemic Bacteriology 1990; 40 (1): 34-39.
15) Nakagawa M, Hirota A, Sakai H and Isogai A. J. Antibiot. 1982: 35:778-782.
16) Nitta K, Fujita N, Yoshimura T, Arai K and Yamamoto U. Chem. Pharm. Bull. (Tokyo) 1983: 31:1528-1533.
17) Raper K B and Fennell D I (1965) The genus *Aspergillus*, Williams and Wilkins, New York; 567-577.
18) Rajasekharan R, Rodrigues R and Reddy S. U.S. Pat. No. 6,277,786.
19) Sankawa U, Ebizuka Y, Noguchi H, Isikawa Y, Kitaghawa S, Yamamoto Y, Kobayashi T and Iitak Y. Tetrahedron 1983: 39:3583-3591.
20) Seifert K A (1990) Isolation of filamentous fungi, In: Isolation of biotechnological organisms from nature (David P L ed), McGraw-Hill, New York; 21-51.
21) Strobel R J and Nakatsukasa W M, J Industrial Microbiology 1993; 11:121-127.
22) Takahashi I, Ojima N, Ogura K and Seto S. Biochemistry 1978: 17:2696-2702.
23) Vinci V A, Hoerner T D, Coffman A D, Schimmel T G, Dabora R L, Kirpekar A C, Ruby C L and Stieber R W. J. Ind. Microbiol. 1991: 8:113-120.
24) Yoo I D, Cho K M, Lee C K, Kim W G. Bioorg Med Chem Lett. 2005 Jan. 17;15(2):353-6.
25) Zhi-hua J, Jian-ping W U, Yuan Z, Xiu C, Li-rong Y and Pei-lin C, J Zhejiang Univ SCIENCE A 2006 7(Suppl. II):366-370.

We claim:

1. Isolated fungal strain capable of producing insecticide, said strain having accession number selected from group consisting of 5394, 5393, 5392, 5391 and 5390 deposited at MTCC, Chandigarh.

2. The isolated fungal strain as claimed in claim 1, wherein the strain belongs to genus *Aspergillus*.

3. The isolated fungal strain as claimed in claim 1, wherein the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07.

4. The isolated fungal strain as claimed in claim 1, wherein the insecticide is spinosyn.

5. A culture of isolated fungal strain capable of producing insecticide, said strain having accession numbers selected from group consisting of 5394, 5393, 5392, 5391 and 5390 deposited at MTCC, Chandigarh.

6. The culture of isolated fungal strain as claimed in claim 5, wherein the strain belongs to genus *Aspergillus*.

7. The culture of isolated fungal strain as claimed in claim 5, wherein the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillius wendtii* IISBC 12 and the strain having accession No.5390 is *Aspergillus terreus* IISBC 07.

8. The culture of isolated fungal strain as claimed in claim 5, wherein the insecticide is spinosyn.

9. A process for production of insecticide from isolated fungal strain having accession number selected from group consisting of 5394, 5393, 5392, 5391 and 5390 deposited at MTCC, Chandigarh, said process comprises step of culturing the isolated fungal strain.

10. The process as claimed in claim 9, wherein the isolated fungal strain belongs to genus *Aspergillus*.

11. The process as claimed in claim 9, wherein the strain having accession No.5394 is *Aspergillus terreus* IISBC 35, the strain having accession No.5393 is *Aspergillus niger* IISBC 28, the strain having accession No.5392 is *Aspergillus glaucus* IISBC 19, the strain having accession No.5391 is *Aspergillus wentii* IISBC 12 and the strain having accession No.5390 is *Aspergillus terreus* IISBC 07.

12. The process as claimed in claim 9, wherein the insecticide is spinosyn.

13. The process as claimed in claim 9, wherein said isolated fungal strain is cultured in a fermentation medium to obtain biomass.

14. The process as claimed in claim 13, wherein said biomass is dried and extracted with an organic solvent in ratio ranging between 1;5 to 1:20.

15. The process as claimed in claim 14, wherein the extraction with organic solvent is followed by constant shaking for 15 to 60 minutes.

16. The process as claimed in claim 14, wherein the organic solvent is selected from a group consisting of methanol, ethyl acetate, acetonitrile, chloroform, dichloromethane and combinations thereof.

17. The process as claimed in claim 14, wherein the extracted biomass is filtered followed by concentration at a temperature ranging from about 30° C. to about 45° C. to obtain the insecticide.

18. A method of cultivation of isolated fungal strain capable of producing insecticide, said strain having accession number selected from group consisting of 5394, 5393, 5392, 5391 and 5390 deposited at MTCC, Chandigarh, wherein the method comprises step of culturing said isolated strain in a static, submerged condition at a temperature ranging from about 25° C. to about 35° C. and pH ranging from about 3 to about 8 for a period ranging from about 2 to about 8 days.

19. The method as claimed in claim 18, wherein the temperature is preferably about 30° C. and the pH is about 4.5.

20. The method as claimed in claim 18, wherein the strain is cultured for a period of about 6 days.

* * * * *